United States Patent
Yamamoto et al.

(10) Patent No.: US 11,989,761 B2
(45) Date of Patent: May 21, 2024

(54) VEHICLE USAGE FEE DETERMINATION SYSTEM AND VEHICLE USAGE FEE DETERMINATION METHOD

(71) Applicant: TOYOTA JIDOSHA KABUSHIKI KAISHA, Aichi-ken (JP)

(72) Inventors: Reiko Yamamoto, Anjo (JP); Gen Fukuyama, Nagoya (JP); Masao Tajima, Toyota (JP); Mikio Inoue, Nagoya (JP)

(73) Assignee: TOYOTA JIDOSHA KABUSHIKI KAISHA, Aichi-Ken (JP)

( * ) Notice: Subject to any disclaimer, the term of this patent is extended or adjusted under 35 U.S.C. 154(b) by 85 days.

(21) Appl. No.: 17/685,319

(22) Filed: Mar. 2, 2022

(65) Prior Publication Data
US 2022/0366466 A1 Nov. 17, 2022

(30) Foreign Application Priority Data
May 12, 2021 (JP) ................................. 2021-081154

(51) Int. Cl.
*G06Q 10/02* (2012.01)
*A61B 5/00* (2006.01)
*A61B 5/18* (2006.01)
*G06Q 30/0283* (2023.01)

(52) U.S. Cl.
CPC ........... *G06Q 30/0283* (2013.01); *A61B 5/18* (2013.01); *A61B 5/4809* (2013.01)

(58) Field of Classification Search
None
See application file for complete search history.

(56) References Cited

U.S. PATENT DOCUMENTS

| | | | | |
|---|---|---|---|---|
| 5,925,082 A | * | 7/1999 | Shimizu | B62D 6/00 180/443 |
| 7,206,631 B2 | * | 4/2007 | Kawachi | A61B 5/18 600/509 |
| 7,915,005 B2 | * | 3/2011 | Shaw | C12Q 1/40 600/573 |
| 9,460,601 B2 | * | 10/2016 | Mimar | G08B 21/06 |
| 10,346,698 B2 | * | 7/2019 | Torii | G06V 20/597 |
| 2006/0103513 A1 | * | 5/2006 | Ihara | H04M 1/72403 348/148 |
| 2013/0218035 A1 | * | 8/2013 | Masuda | A61B 5/0245 600/508 |
| 2019/0114939 A1 | * | 4/2019 | Kielbasa | G09B 19/00 |
| 2020/0219615 A1 | * | 7/2020 | Rabin | G16H 50/30 |

FOREIGN PATENT DOCUMENTS

| | | | |
|---|---|---|---|
| JP | 2010149757 A | 7/2010 | |
| WO | WO-9967757 A1 | * 12/1999 | ........... A61B 3/0066 |
| WO | WO-2007138265 A2 | * 12/2007 | ........... G08G 1/0175 |

* cited by examiner

*Primary Examiner* — Tonya Joseph
(74) *Attorney, Agent, or Firm* — HAUPTMAN HAM, LLP

(57) ABSTRACT

A vehicle usage fee determination system includes a reception unit that receives a usage application by a user who has an intention to drive a vehicle, a wakefulness level estimation unit that estimates a wakefulness level of the user, and a fee determination unit that sets a usage fee of the vehicle when a target wakefulness level that is the wakefulness level at a time a first predetermined time before a scheduled driving start time of the vehicle by the user is a predetermined value to be equal to or less than a usage fee of the vehicle when the target wakefulness level is lower than the predetermined value.

20 Claims, 10 Drawing Sheets

FIG. 6

| WAKEFULNESS LEVEL | FEE COEFFICIENT |
|---|---|
| WAKEFULNESS LEVEL 5 | 0.75 |
| WAKEFULNESS LEVEL 4 | 0.8 |
| WAKEFULNESS LEVEL 3 | 0.9 |
| WAKEFULNESS LEVEL 2 | 0.9 |
| WAKEFULNESS LEVEL 1 | 1.0 |
| SLEEP LEVEL 1 | 1.1 |
| SLEEP LEVEL 2 | 1.2 |
| SLEEP LEVEL 3 | 1.3 |
| SLEEP LEVEL 4 | 1.4 |
| SLEEP LEVEL 5 | 1.5 |

FIG. 12

START
↓
S30: HAS COUNT NUMBER BEEN RECEIVED? — NO →
↓ YES
S31: IS COUNT NUMBER ONE OR MORE? — NO →
↓ YES
S32: PERFORM FEE INCREASING PROCESS
↓
S33: TRANSMIT DATA REGARDING CORRECTION FEE TO MOBILE TERMINAL
↓
END

FIG. 13

| COUNT NUMBER | FEE INCREASING COEFFICIENT |
|---|---|
| 1 | 1.1 |
| 2 | 1.2 |
| 3 | 1.3 |
| ⋮ | ⋮ |

| | | |
|---|---|---|
| NORMAL FEE | ⋯ | XYXZ YEN |
| FEE COEFFICIENT | ⋯ | 1.2 |
| CONTRACT FEE | ⋯ | XZYY YEN |

VEHICLE USAGE FEE DETERMINATION SYSTEM AND VEHICLE USAGE FEE DETERMINATION METHOD

CROSS-REFERENCE TO RELATED APPLICATION

This application claims priority to Japanese Patent Application No. 2021-081154 filed on May 12, 2021, incorporated herein by reference in its entirety.

BACKGROUND

1. Technical Field

The present disclosure relates to a vehicle usage fee determination system and a vehicle usage fee determination method.

2. Description of Related Art

The following Japanese Unexamined Patent Application Publication No. 2010-149757 (JP 2010-149757 A) discloses an disclosure in which maintenance of a wakefulness state of a driver is supported by selecting and playing music while learning a psychological effect of sound on the driver.

SUMMARY

The above JP 2010-149757 A has room for improvement in encouraging a driver who pays a fee to drive a vehicle to get sufficient sleep before boarding the vehicle.

In consideration of the above fact, an object of the present disclosure is to provide a vehicle usage fee determination system and a vehicle usage fee determination method capable of encouraging a driver who pays a fee to drive a vehicle to get sufficient sleep before boarding the vehicle.

A vehicle usage fee determination system according to a first aspect of the present disclosure includes a reception unit that receives a usage application by a user who has an intention to drive a vehicle, a wakefulness level estimation unit that estimates a wakefulness level of the user, and a fee determination unit that sets a usage fee of the vehicle when a target wakefulness level that is the wakefulness level at a time a first predetermined time before a scheduled driving start time of the vehicle by the user is a predetermined value to be equal to or lower than a usage fee of the vehicle when the target wakefulness level is lower than the predetermined value.

The vehicle usage fee determination system according to the first aspect includes the reception unit that receives the usage application by the user who has the intention to drive the vehicle, and the wakefulness level estimation unit that estimates the wakefulness level of the user. Further, the fee determination unit of the vehicle usage fee determination system sets the usage fee of the vehicle when the target wakefulness level that is the wakefulness level at the time a first predetermined time before the scheduled driving start time of the vehicle by the user is the predetermined value to be equal to or lower than the usage fee of the vehicle when the target wakefulness level is lower than the predetermined value. As a result, the vehicle usage fee determination system according to the first aspect can encourage the user who pays a fee to drive the vehicle to get sufficient sleep before boarding the vehicle.

In the first aspect, a wearable device that is able to be worn by the user may include the wakefulness level estimation unit.

In the above aspect, the wakefulness level estimation unit of the wearable device estimates the wakefulness level of the user. Therefore, according to the above aspect, it is possible to reduce a labor to be required for the user to estimate the wakefulness level.

In the above aspect, in a case where a special condition to be satisfied when a state in which the wakefulness level of the user during driving the vehicle is lower than a predetermined threshold value continues for a second predetermined time or longer is satisfied, the fee determination unit may set the usage fee of the vehicle high as compared with a case where the special condition is not satisfied.

In the above aspect, the special condition is satisfied when the state in which the wakefulness level of the user during driving the vehicle is lower than the predetermined threshold value continues for the second predetermined time or longer. Then, when the special condition is satisfied, the fee determination unit sets the usage fee higher than when the special condition is not satisfied. Therefore, the vehicle usage fee determination system according to the above aspect can encourage the user who drives the vehicle in a state of the low wakefulness level to temporarily stop driving the vehicle.

A vehicle usage fee determination method according to a second aspect of the present disclosure includes a step of receiving a usage application by a user who has an intention to drive a vehicle, a step of estimating a wakefulness level of the user, and a step of setting a usage fee of the vehicle when a target wakefulness level that is the wakefulness level at a time a first predetermined time before a scheduled driving start time of the vehicle by the user is a predetermined value to be equal to or lower than a usage fee of the vehicle when the target wakefulness level is lower than the predetermined value.

As described above, the vehicle usage fee determination system and the vehicle usage fee determination method according to the present disclosure has a superior effect that the user who pays a fee to drive the vehicle can be encouraged to get sufficient sleep before boarding the vehicle.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein:

FIG. 6 is a diagram showing a fee coefficient map recorded in a read only memory (ROM) of the management server;

FIG. 12 is a flowchart showing a process executed by the management server;

FIG. 13 is a diagram showing a fee increasing coefficient map recorded in the ROM of the management server; and FIG. 14 is a diagram showing a correction fee determined by the fee determination unit while performing the fee reduction process.

DETAILED DESCRIPTION OF EMBODIMENTS

Hereinafter, an embodiment of a vehicle usage fee determination system 10 (hereinafter simply referred to as a system 10) and a vehicle usage fee determination method according to the present disclosure will be described with reference to the drawings.

Figure 1:
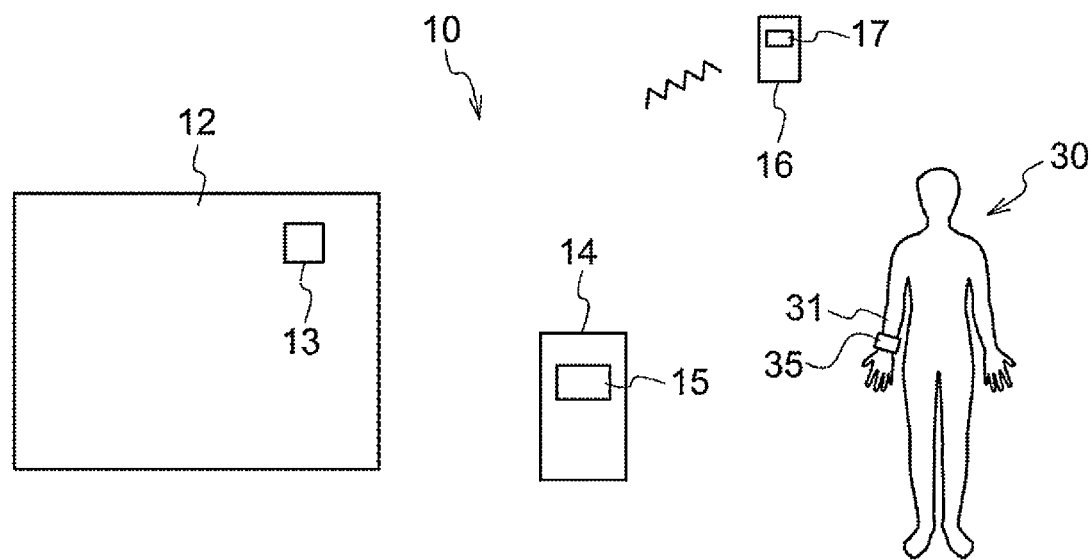
FIG. 1 is an overall view of a vehicle usage fee determination system according to an embodiment.
Figure 1:
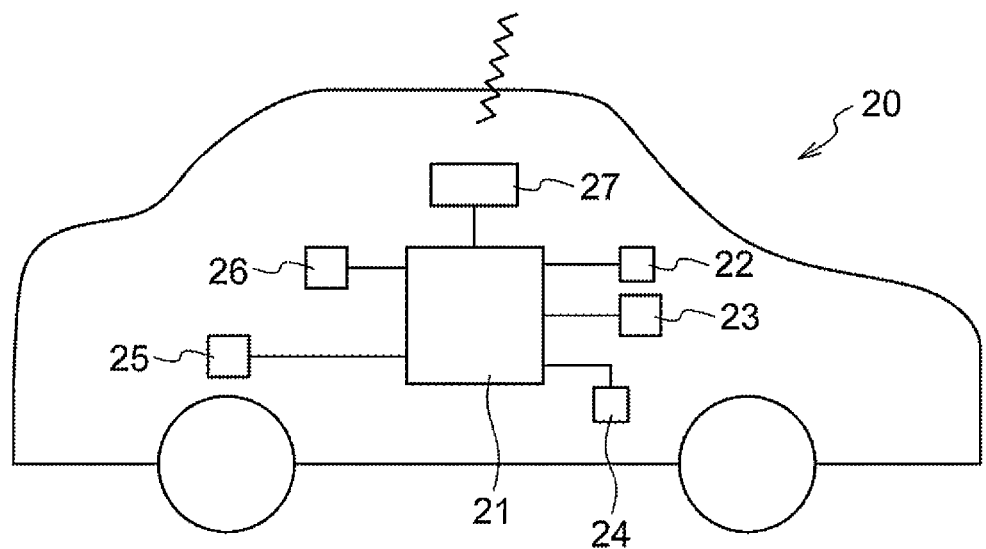

FIG. 1 shows an overall configuration of the system 10 according to the embodiment. The system 10 includes a management server 12, an operation terminal 14, a mobile terminal 16, and a wearable device 35. The management server 12 and the operation terminal 14 are installed, for example, in a store of a rental car company that owns a plurality of vehicles 20. In the present embodiment, this store is installed in an airport. The mobile terminal 16 is, for example, a smartphone or a tablet computer. The wearable device 35 is attached to an arm 31 of a user 30 who uses the vehicle 20 owned by the rental car company. It is assumed that the user 30 of the present embodiment has come to the airport by using an aircraft from a country different from a country in which the airport is located.

Figure 2:
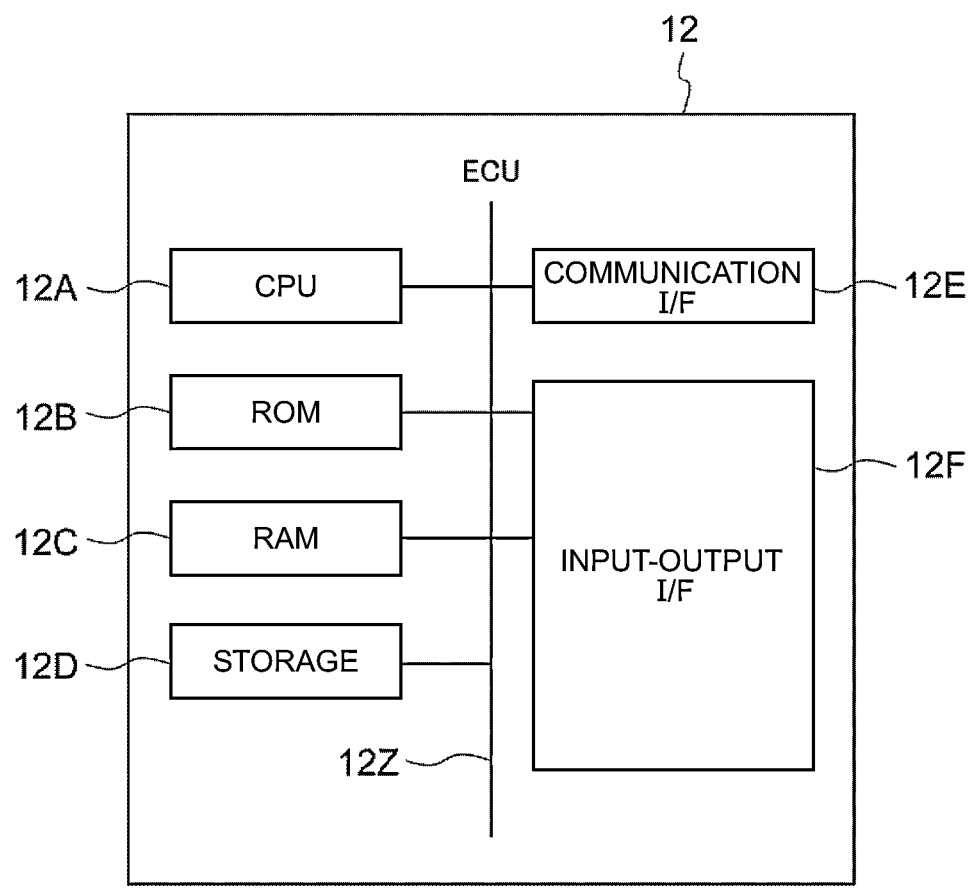
FIG. 2 is a control block diagram of a management server of the vehicle usage fee determination system shown in FIG. 1.

The management server 12 shown in FIG. 2 is configured to include a central processing unit (CPU: processor) 12A, a read-only memory (ROM) 12B, a random access memory (RAM) 12C, a storage 12D, a communication interface (I/F) 12E, and an input-output I/F 12F. The CPU 12A, the ROM 12B, the RAM 12C, the storage 12D, the communication I/F 12/E, and the input-output I/F 12F are connected so as to be able to communicate with each other via a bus 12Z. The management server 12 can acquire information of the date and time from a timer (not shown).

The CPU 12A is a central processing unit that executes various programs and that controls various units. That is, the CPU 12A reads the program from the ROM 12B or the storage 12D and executes the program using the RAM 12C as a work area. The CPU 12A controls each configuration and performs various arithmetic processes in accordance with the program recorded in the ROM 12B or the storage 12D.

The ROM 12B stores various programs and various data. The RAM 12C temporarily stores a program or data as a work area. The storage 12D is composed of a storage device such as a hard disk drive (HDD) or a solid state drive (SSD), and stores various programs and various data. The communication I/F 12E is an interface for the management server 12 to communicate with other devices. The input-output I/F 12F is an interface for communicating with various devices. For example, a wireless communication device 13 provided in the management server 12 is connected to the input-output I/F 12F.

Figure 3:
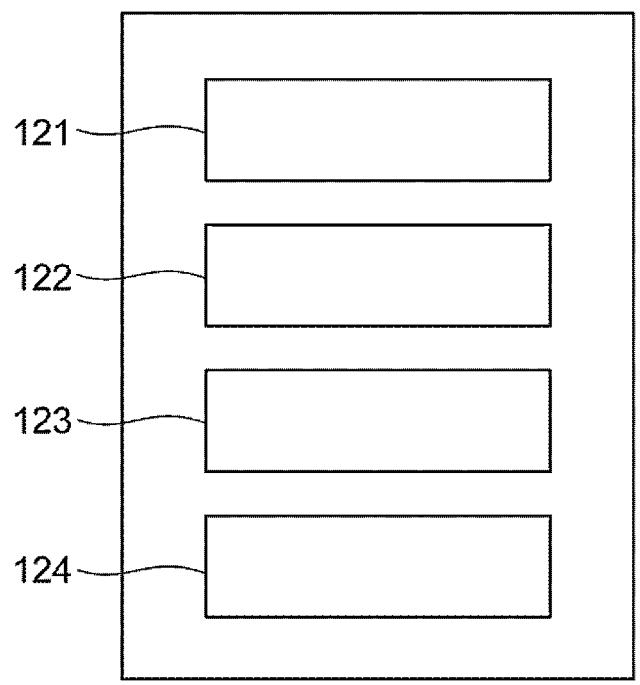
FIG. 3 is a functional block diagram of the management server shown in FIG. 2.

FIG. 3 shows an example of a functional configuration of the management server 12 by a block diagram. The management server 12 includes a transmission-reception unit 121, a reception unit 122, a fee determination unit 123, and a wireless control unit 124. The transmission-reception unit 121, the reception unit 122, the fee determination unit 123, and the wireless control unit 124 are realized by the CPU 12A reading and executing the program stored in the ROM 12B.

The transmission-reception unit 121 transmits and receives information to and from the operation terminal 14 (transmission-reception unit 141) via a Local Area Network (LAN).

The reception unit 122 receives a usage application by the user 30 who has an intention to drive a vehicle.

The fee determination unit 123 determines a usage fee (contract fee, correction fee) when the user 30 uses the vehicle 20.

The wireless control unit 124 controls the wireless communication device 13. That is, the wireless control unit 124 controls the wireless communication device 13, so that the wireless communication device 13 executes wireless communication between the mobile terminal 16 and the vehicle 20.

The operation terminal 14 is configured to include a CPU, a ROM, a RAM, a storage, a communication I/F, and an input-output I/F. The CPU, the ROM, the RAM, the storage, the communication I/F, and the input-output I/F of the operation terminal 14 are connected to each other so as to be able to communicate with each other via a bus. The operation terminal 14 can acquire information of the date and time from a timer (not shown). The operation terminal 14 is provided with a display unit 15 including a touch panel. The display unit 15 is connected to the input-output I/F of the operation terminal 14.

The mobile terminal 16 shown in FIG. 1 is owned by the user 30 of the system 10. The mobile terminal 16 includes a display unit 17 including a touch panel. The mobile terminal 16 is configured to include a CPU, a ROM, a RAM, a storage, a communication I/F, and an input-output I/F. The CPU, the ROM, the RAM, the storage, the communication I/F, and the input-output I/F are connected to each other so as to be able to communicate with each other via a bus. The mobile terminal 16 can acquire information of the date and time from a timer (not shown). A wireless communication device (not shown) of the mobile terminal 16 can wirelessly communicate with the wireless communication device 13. Further, a rental car reservation application that is software created by the rental car company is installed on the mobile terminal 16.

Figure 4:
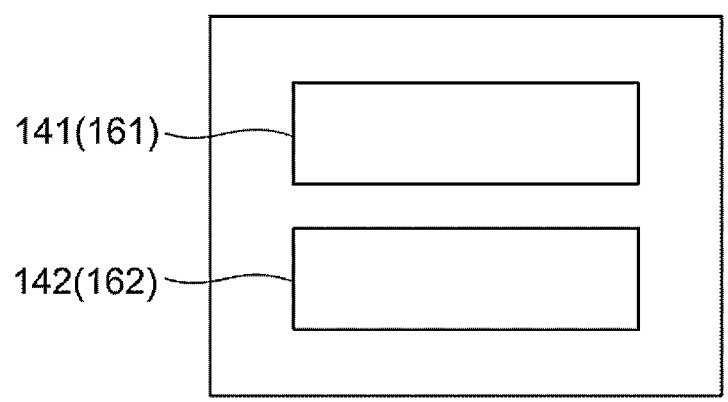
FIG. 4 is a functional block diagram of an operation terminal (mobile terminal) shown in FIG. 1.

FIG. 4 shows an example of a functional configuration of the operation terminal 14 and the mobile terminal 16 by a block diagram. The operation terminal 14 includes the transmission-reception unit 141 and a display unit control unit 142 as a functional configuration. Similarly, the mobile terminal 16 includes a wireless control unit 161 and a display unit control unit 162 as a functional configuration. The transmission-reception unit 141, the wireless control unit 161, and the display unit control units 142 and 162 are realized by the CPU reading and executing the program stored in the ROM.

The transmission-reception unit 141 transmits and receives information to and from the transmission-reception unit 121 of the management server 12 via the LAN. The wireless communication device controlled by the wireless control unit 161 performs wireless communication with the wireless control unit 124 (wireless communication device 13) of the management server 12 and the vehicle 20.

The display unit control unit 142 controls the display unit 15. That is, the display unit control unit 142 causes the display unit 15 to display, for example, the information received from the transmission-reception unit 121 by the transmission-reception unit 141 and the information input via the touch panel. Further, the display unit control unit 142 transmits the information input via the touch panel of the display unit 15 to the transmission-reception unit 141, and causes the transmission-reception unit 141 to transmit the information to the transmission-reception unit 121.

The display unit control unit 162 controls the display unit 17. That is, the display unit control unit 162 causes the display unit 17 to display, for example, the information received by the wireless communication device (wireless control unit 161) from the wireless communication device 13 (wireless control unit 124) and the vehicle 20 and the information input via the touch panel of the mobile terminal 16. Further, the display unit control unit 162 transmits the information input via the touch panel to the wireless control unit 161 and the wireless communication device transmits the information to the wireless communication device 13 and the vehicle 20.

FIG. 1 shows the vehicle 20 owned by the rental car company. An identification (ID) representing each vehicle is given to each vehicle owned by the rental car company.

The vehicle 20 includes an electronic control unit (ECU) 21, a camera 22, a display 23, a speaker 24, a wheel speed sensor 25, a Global Positioning System (GPS) receiver 26, and a wireless communication device 27. The camera 22, the display 23, the speaker 24, the wheel speed sensor 25, the GPS receiver 26, and the wireless communication device 27 are connected to the ECU 21. The ECU 21 is configured to include a CPU, a ROM, a RAM, a storage, a communication I/F, and an input-output I/F. The CPU, the ROM, the RAM, the storage, the communication I/F, and the input-output I/F of the ECU 21 are connected to each other so as to be able to communicate with each other via a bus. The ECU 21 can acquire information of the date and time from a timer (not shown).

The camera 22 is provided on the rear surface of a front windshield (not shown) of the vehicle 20. The camera 22 can capture an image of the face and body of the user (driver) 30 seated in a driver's seat (not shown) of the vehicle 20.

The display 23 including a touch panel is provided on an instrument panel (not shown) of the vehicle 20.

The speaker 24 can output sound.

The wheel speed sensor 25 detects wheel speeds of four wheels (not shown) provided in the vehicle 20.

The GPS receiver 26 acquires position information (latitude, longitude, etc.) of a point where the vehicle 20 is traveling based on a GPS signal transmitted from an artificial satellite at a predetermined cycle.

Figure 5:
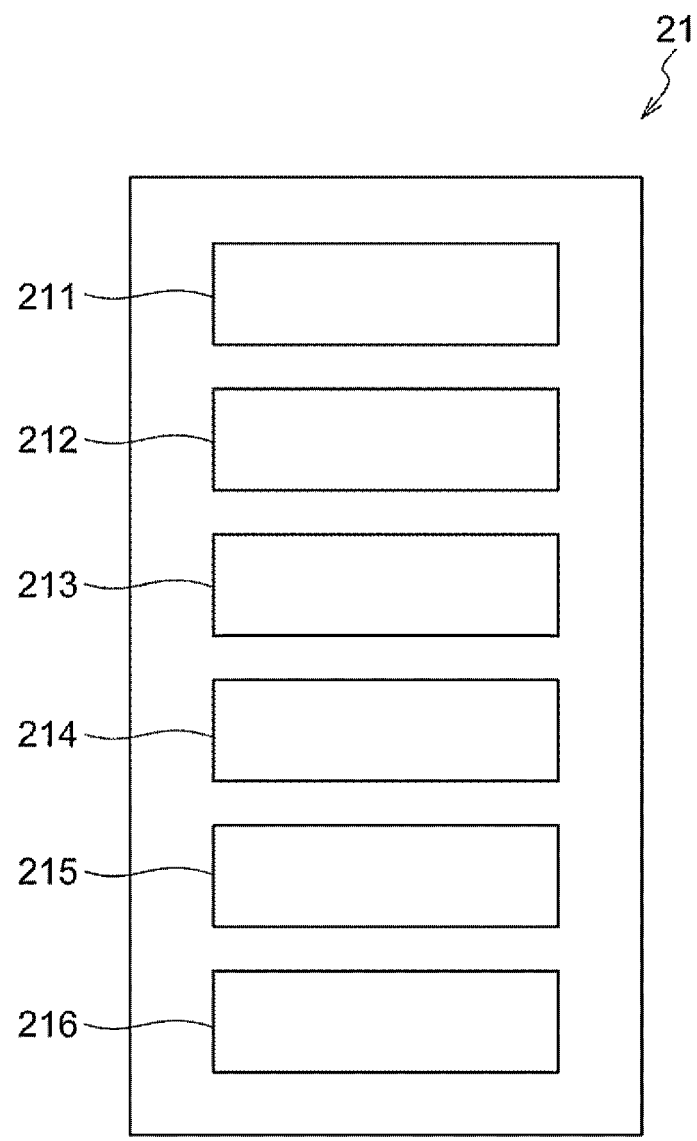
FIG. 5 is a functional block diagram of an electronic control unit (ECU) of a vehicle shown in FIG. 1.

FIG. 5 shows an example of a functional configuration of the ECU 21 by a block diagram. The ECU 21 includes a wakefulness level estimation unit 211, a warning generation unit 212, a display unit control unit 213, a speaker control unit 214, a count unit 215, and a wireless control unit 216 as functional configurations. The wakefulness level estimation unit 211, the warning generation unit 212, the display unit control unit 213, the speaker control unit 214, the count unit 215, and the wireless control unit 216 are realized by the CPU of the ECU 21 reading and executing the program stored in the ROM.

The wakefulness level estimation unit 211 determines a wakefulness level of the user 30 based on a state of the eyes and the like of the user 30 seated in the driver's seat. The state of the eyes and the like is included in the image data captured by the camera 22. For example, the wakefulness level estimation unit 211 measures a degree to which the eyelids of the user 30 are open and a cycle of opening and closing the eyelids from the images of surrounding portions of the eyes of the user 30. Further, the wakefulness level estimation unit 211 estimates the wakefulness level of the user 30 based on the degree to which the eyelids of the user 30 are open and the cycle of opening and closing the eyelids. The "wakefulness level" in the present specification and claims includes a wakefulness level when a human is awake and a sleep level (sleep depth) when the human is in a sleeping state.

A fee coefficient map 28 shown in FIG. 6 shows a relationship between the wakefulness level of the user 30 at a target time to be described later and a fee coefficient to be multiplied by a contract fee that is a fee to be charged when the user rents a vehicle. The fee coefficient map 28 is recorded in the ROM of the ECU 21. In the fee coefficient map 28, the wakefulness level and the sleep level (sleep depth) are each defined in five levels. The higher the wakefulness level of the user 30 is, the larger the number of the wakefulness level becomes. The higher the sleep depth of the target user 30 is, the larger the number of the sleep level (sleep depth) becomes. The sleep level 1 is a level corresponding to rapid eye movement (REM) sleep. The sleep levels 2 to 5 are levels corresponding to non-rapid eye movement (Non-REM) sleep. The sleep levels 2 and 3 correspond to the Non-REM sleep in stages 1 and 2, respectively. The sleep levels 4 and 5 correspond to the Non-REM sleep (slow wave sleep) in stage 3 and 4, respectively.

As will be described later, the warning generation unit 212 generates data representing a warning that can be output by the display 23 and the speaker 24.

The display unit control unit 213 controls the display 23. That is, the display unit control unit 213, for example, causes the display 23 to display the information received by the wireless communication device 27 from the wireless communication device 13 and the mobile terminal 16 and the information input via the touch panel. Further, the display unit control unit 213 transmits the information input via the touch panel of the display 23 to the wireless communication device 27, and causes the wireless communication device 27 to transmit the information to the wireless communication device 13 and the mobile terminal 16.

The speaker control unit 214 controls the speaker 24.

The count unit 215 counts up when a special condition to be described later is satisfied.

The wireless control unit 216 controls the wireless communication device 27. That is, the wireless control unit 216 controls the wireless communication device 27, so that the wireless communication device 27 executes wireless communication between the management server 12 (wireless communication device 13) and the mobile terminal 16.

As shown in FIG. 1, the wearable device 35 is attached to the arm 31 of the user 30. The wearable device 35 includes a wireless communication device (not shown) and a detection unit (not shown). The detection unit detects at least one of the heart rate and the blood pressure of the user 30. Further, the wearable device 35 is configured to include a CPU, a ROM, a RAM, a storage, a communication I/F, and an input-output I/F. The CPU, the ROM, the RAM, the storage, the communication I/F, and the input-output I/F of the wearable device 35 are connected to each other so as to be able to communicate with each other via a bus.

Figure 7:
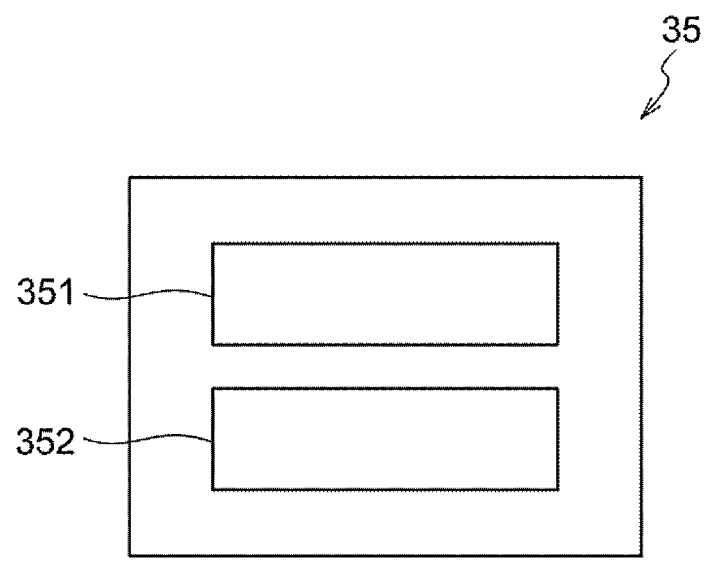
FIG. 7 is a functional block diagram of a wearable device shown in FIG. 1.

FIG. 7 shows an example of a functional configuration of the wearable device 35 in a block diagram. The wearable device 35 includes a wakefulness level estimation unit 351 and a wireless control unit 352 as functional configurations. The wakefulness level estimation unit 351 and the wireless control unit 352 are realized by the CPU of the wearable device 35 reading and executing the program stored in the ROM. The wearable device 35 can acquire information of the date and time from a timer (not shown).

The wakefulness level estimation unit 351 estimates the wakefulness level of the user 30 based on a detection value transmitted from the detection unit of the wearable device 35. The wakefulness level estimation unit 351 determines that the lower the heart rate and blood pressure, the higher the sleep level (the lower the wakefulness level), and the higher the heart rate and blood pressure, the lower the sleep level (the higher the wakefulness level). Similarly to the wakefulness level estimation unit 211, the wakefulness level estimation unit 351 estimates each of the wakefulness level and the sleep level (sleep depth) of the user 30 in five levels.

The wireless control unit 352 controls a wireless communication device (not shown) of the wearable device 35. That is, the wireless control unit 352 controls the wireless communication device, so that the wireless communication device of the wearable device 35 executes wireless communication with the wireless communication device of the mobile terminal 16. That is, the wireless control unit 352 controls the wireless communication device of the wearable device 35, so that the information regarding the wakefulness level of the user 30 estimated by the wakefulness level estimation unit 351 is transmitted from the wearable device 35 to the mobile terminal 16 while being associated with the time information acquired by the timer of the wearable device 35. The mobile terminal 16 causes the storage to record the wakefulness level data that is data related to the received wakefulness level, and the time information.

Operation and Effects

Next, the operation and effects of the present embodiment will be described.

First, a flow of a process executed by the management server 12 according to the present embodiment will be described with reference to the flowcharts of FIGS. 8, 11 and 12.

Figure 8:
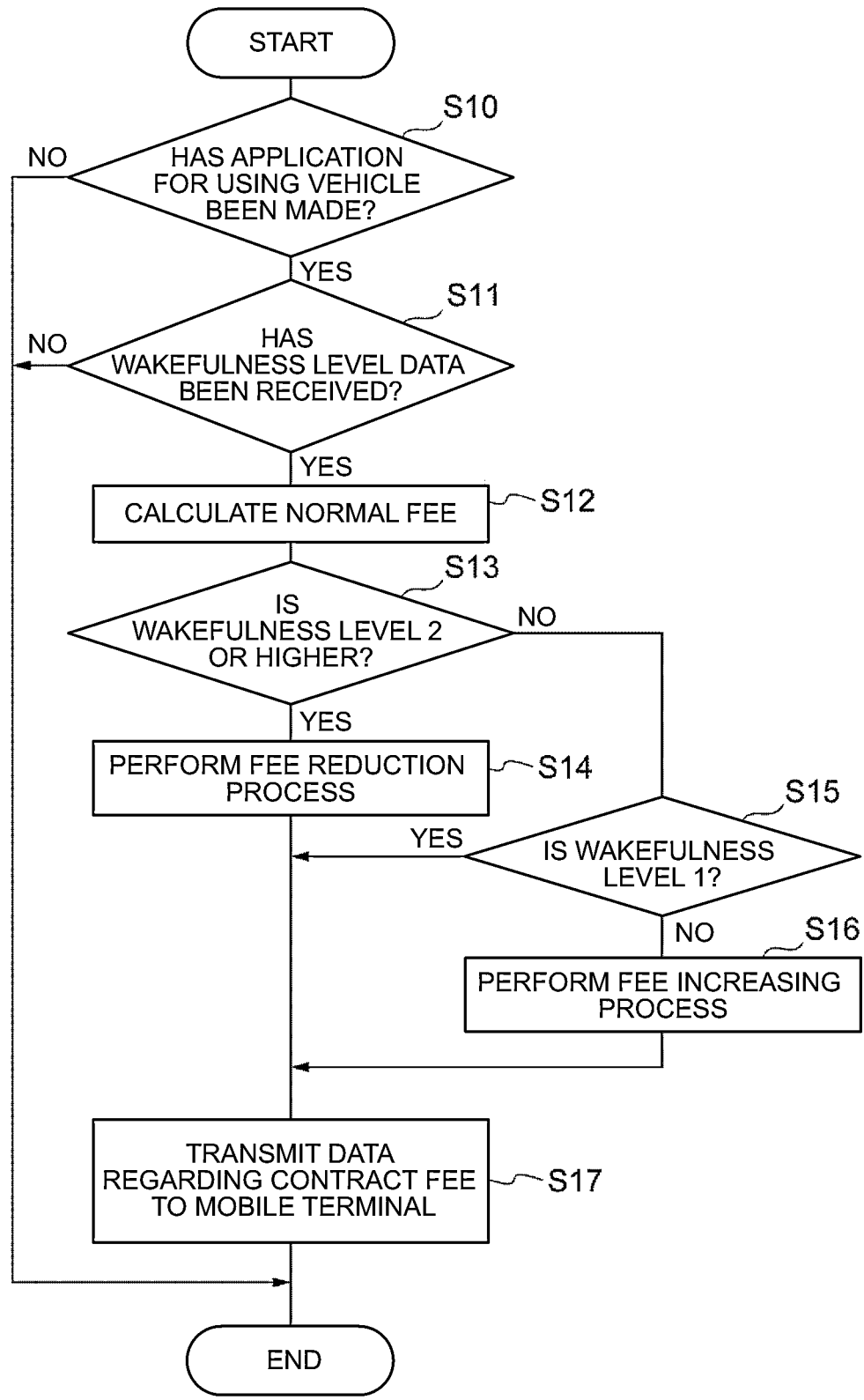
FIG. 8 is a flowchart showing a process executed by the management server.

When an ignition switch (not shown) of the vehicle 20 is switched from the OFF position to the ON position, the management server 12 repeatedly executes the process of the flowchart of FIG. 8 every time a predetermined time elapses.

First, in step S10, the reception unit 122 of the management server 12 determines whether an application for using the vehicle 20 has been made from the operation terminal 14 (display unit 15) or the mobile terminal 16 (display unit 17). In other words, the reception unit 122 determines whether usage application data that is data representing usage application has been transmitted from the operation terminal 14 to the transmission-reception unit 121 or from the mobile terminal 16 to the wireless communication device 13.

When the determination result is Yes in step S10, the management server 12 proceeds to step S11, and determines whether the reception unit 122 has received information regarding a target wakefulness level that is a wakefulness level of the user 30 at a target time. Here, the "target time" is a time a first predetermined time before the scheduled driving start time that is the time when the user 30 starts using the vehicle 20. The first predetermined time is, for example, 20 minutes. The data regarding the first predetermined time is recorded in the ROM 12B of the management server 12. Further, the scheduled driving start time is determined by the reception unit 122 based on the wishes of the user 30 and the current usage status of the vehicle 20. For example, when the user 30 makes a usage application using the mobile terminal 16, the wakefulness level data (time information) is transmitted from the mobile terminal 16 to the wireless communication device 13 of the management server 12 together with the usage application data, and the wakefulness level data is recorded in the storage 12D. Further, when the user 30 makes a usage application using the operation terminal 14, the wakefulness level data (time information) is transmitted from the operation terminal 14 to the wireless communication device 13 of the management server 12, and the wakefulness level data is recorded in the storage 12D.

When the determination result is Yes in step S11, the management server 12 proceeds to step S12, and the fee determination unit 123 calculates a normal fee based on a type of vehicle and a usage time that the user 30 desires.

The management server 12 that has ended the process of step S12 proceeds to step S13, and the fee determination unit 123 determines whether the data regarding the target wakefulness level of the user 30 is data representing the wakefulness level of "wakefulness level 2" or higher. In other words, the fee determination unit 123 determines whether the data representing the target wakefulness level of the user 30 is the data representing any one of the wakefulness levels 2 to 5.

When the determination result is Yes in step S13, the management server 12 proceeds to step S14, and the fee determination unit 123 performs a fee reduction process from the normal fee while referring to the fee coefficient map 28. Specifically, the fee determination unit 123 multiplies the normal fee by a fee coefficient corresponding to the target wakefulness level. For example, when the data representing the target wakefulness level represents the wakefulness level 2, the fee determination unit 123 multiplies the normal fee by 0.9 to calculate a contract fee that is a reduced fee.

On the other hand, when the determination result is No in step S13, the management server 12 proceeds to step S15, and the fee determination unit 123 determines whether the data representing the target wakefulness level of the user 30 represents the wakefulness level 1.

The fee coefficient when the determination result is Yes in step S15 is 1.0. Therefore, in this case, the fee reduction process and the fee increasing process for the normal fee calculated in step S12 are not performed. That is, the contract fee in this case is the same as the normal fee.

On the other hand, when the determination result is No in step S15, the management server 12 proceeds to step S16, and the fee determination unit 123 performs the fee increasing process from the normal fee while referring to the fee coefficient map 28. Specifically, the fee determination unit 123 multiplies the normal fee by a fee coefficient corresponding to the sleep level indicated by the data representing the target wakefulness level. For example, when the data representing the target wakefulness level represents the sleep level 3, the fee determination unit 123 multiplies the normal fee by 1.3 to calculate a contract fee that is an increased fee.

Figure 9:
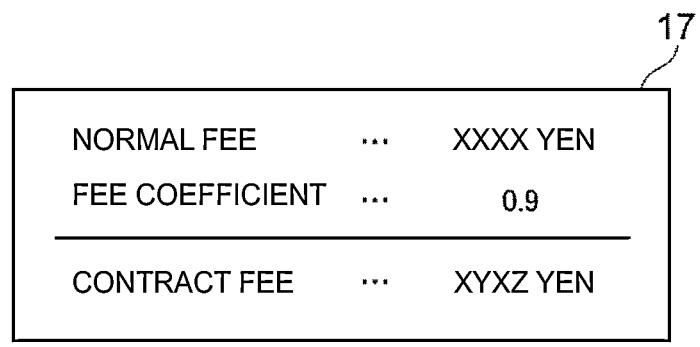
FIG. 9 is a diagram showing a contract fee determined by a fee determination unit of the management server while performing a fee reduction process.
Figure 10:
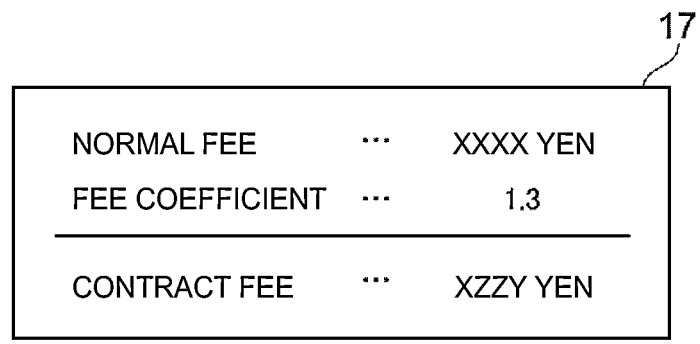
FIG. 10 is a diagram showing a contract fee determined by the fee determination unit while performing a fee increasing process.

The management server 12 proceeds to step S17 when the management server 12 ends the processes of steps S14 and S16 or when the determination result is Yes in step S15. In step S17, the wireless control unit 124 controls the wireless communication device 13 to transmit data regarding the determined contract fee to the wireless communication device of the mobile terminal 16. Further, the fee determination unit 123 causes the ROM 12B to record data regarding the determined contract fee. Therefore, when the process of step S14 is performed, as shown in FIG. 9, the normal fee, the fee coefficient, and the contract fee are displayed on the display unit 17 of the mobile terminal 16. Further, when the process of step S16 is performed, as shown in FIG. 10, the normal fee, the fee coefficient, and the contract fee are displayed on the display unit 17 of the mobile terminal 16. Although not shown, when the determination result is Yes in step S15, the normal fee is displayed on the display unit 17 as the contract fee.

The management server 12 temporarily ends the process of the flowchart of FIG. 8 when the management server 12 ends the process of step S17 or the determination result is No in steps S10 and S11.

Figure 11:
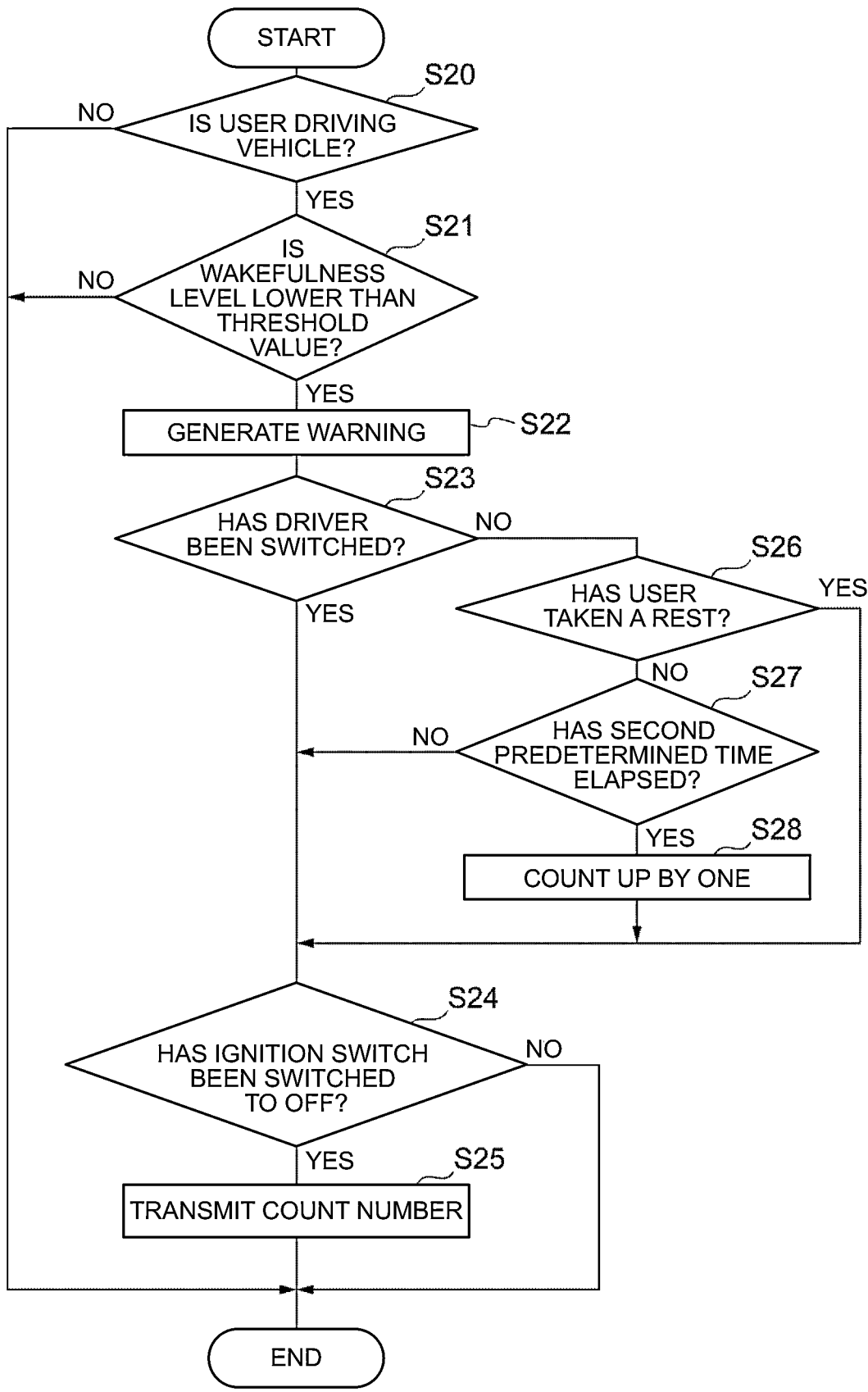
FIG. 11 is a flowchart showing a process executed by the ECU of the vehicle shown in FIG. 1.

When the ignition switch of the vehicle 20 is switched from the OFF position to the ON position, the ECU 21 of the vehicle 20 repeatedly executes the process of the flowchart of FIG. 11 every time a predetermined time elapses.

First, in step S20, the ECU 21 determines whether the user 30 is driving the vehicle 20 based on information on the wheel speed transmitted from the wheel speed sensor 25, position information transmitted from the GPS receiver 26, and image data transmitted from the camera 22.

When the determination result is Yes in step S20, the ECU 21 proceeds to step S21, and determines whether the wakefulness level of the user 30 determined by the wakefulness level estimation unit 211 is lower than a predetermined threshold value based on the image data captured by the camera 22. In the present embodiment, this threshold value is wakefulness level 1. That is, the wakefulness level estimation unit 211 determines whether the wakefulness level of the user 30 is any of the sleep levels 1 to 5. The data regarding this threshold value is recorded in the ROM of the ECU 21.

When the determination result is Yes in step S21, the ECU 21 proceeds to step S22, and the warning generation unit 212 generates data representing a warning that can be output by the display 23 and the speaker 24. Further, the display unit control unit 213 controls the display 23 to cause the display 23 to display the information represented by this data. For example, the display 23 displays the message "Please switch a driver or take a rest". Further, the speaker control unit 214 controls the speaker 24 to cause the speaker 24 to utter the above message.

The management server 12 that has ended the process of step S22 proceeds to step S23, and the warning generation unit 212 determines whether the vehicle 20 has temporarily stopped and the driver has been switched based on the data received from the camera 22, the wheel speed sensor 25, and the GPS receiver 26.

When the determination result is Yes in step S23, the ECU 21 proceeds to step S24, and the wireless control unit 216 determines whether the ignition switch has been switched to the OFF position.

When the determination result is Yes in step S24, the ECU 21 proceeds to step S25, and the wireless control unit 216 controls the wireless communication device 27 to transmit data related to the count number from the wireless communication device 27 to the management server 12 (wireless communication device 13). The initial value of the count number is "zero".

On the other hand, when the determination result is No in step S23, the ECU 21 proceeds to step S26, and the warning generation unit 212 determines whether the vehicle 20 has temporarily stopped and the user 30 has taken a rest based on the data received from the camera 22, the wheel speed sensor 25, and the GPS receiver 26.

When the determination result is Yes in step S26, the ECU 21 proceeds to step S24.

On the other hand, when the determination result is No in step S26, the ECU 21 proceeds to step S27, and the fee determination unit 123 determines whether the second predetermined time has elapsed since the process of step S22 was executed, based on information from the timer. That is, the fee determination unit 123 determines whether a state in which the wakefulness level of the user 30 is lower than the threshold value has continued for the second predetermined time or longer. In the present embodiment, this second predetermined time is five minutes. Data regarding this second predetermined time is recorded in the ROM of the ECU 21.

When the determination result is Yes in step S27, a predetermined special condition is satisfied. Then, when the special condition is satisfied, the ECU 21 proceeds to step S28, and the count unit 215 counts up.

The ECU 21 that has ended the process of step S28 proceeds to step S24. The ECU 21 that has determined Yes in step S24 proceeds to step S25, and the wireless control unit 216 controls the wireless communication device 27 to transmit the data related to the count number from the wireless communication device 27 to the management server 12 (wireless communication device 13).

When the ECU 21 ends the process of step S25, or the determination result is NO in steps S20 and S21, the ECU 21 temporarily ends the process of the flowchart of FIG. 11.

When the ignition switch is switched from the OFF position to the ON position, the management server 12 repeatedly executes the process of the flowchart of FIG. 12 every time a predetermined time elapses.

First, in step S30, the fee determination unit 123 of the management server 12 determines whether the wireless communication device 13 has received data regarding the count number from the wireless communication device 27.

When the determination result is Yes in step S30, the management server 12 proceeds to step S31, and the fee determination unit 123 determines whether the count number represented by the received data is one or more.

When the determination result is Yes in step S31, the management server 12 proceeds to step S32, and the fee determination unit 123 performs a fee increasing process with respect to the contract fee while referring to a fee increasing coefficient map 29 shown in FIG. 13. Specifically, the fee determination unit 123 determines a fee increasing coefficient based on the count number represented by the data received by the wireless communication device 13 and the fee increasing coefficient map 29. Further, the fee determination unit 123 multiplies the contract fee recorded in the ROM 12B in step S17 of FIG. 8 by the determined fee increasing coefficient. For example, when the count number is "two", the fee determination unit 123 multiplies the contract fee by 1.2 to calculate a correction fee that is an increased fee.

The ECU 21 that has ended the process of step S32 proceeds to step S33 and transmits data related to the correction fee to the wireless communication device of the mobile terminal 16. Further, the fee determination unit 123 causes the ROM 12B to record the data regarding the determined correction fee. Therefore, when the process of step S33 is performed, as shown in FIG. 14, the contract fee, the fee increasing coefficient, and the correction fee are displayed on the display unit 17 of the mobile terminal 16.

When the ECU 21 ends the process of step S33, or the determination result is NO in steps S30 and S31, the ECU 21 temporarily ends the process of the flowchart of FIG. 12.

As described above, in the system 10 and the vehicle usage fee determination method according to the present embodiment, the wakefulness level estimation unit 211 estimates a target wakefulness level that is a wakefulness level of the user 30 at a target time first predetermined time before the scheduled driving start time that is a time when the user 30 starts using the vehicle 20. Then, the fee determination unit 123 sets the usage fee (contract fee) of the vehicle 20 when the target wakefulness level is a predetermined value to be equal to or less than the usage fee when the target wakefulness level is lower than the predetermined value. That is, in the fee coefficient map 28 shown in FIG. 6, the fee coefficient when the wakefulness level is a predetermined value is equal to or less than the fee coefficient when the wakefulness level is lower than the predetermined value. In general, the wakefulness level at the current time correlates with the sleep state several hours before the current time. For example, the user 30 who was in a sleep state with a high sleep depth several hours before the current time is likely to have a high wakefulness level at the current time. Therefore, in order to increase the wakefulness level at the target time and reduce the usage fee (contract fee) of the vehicle 20, the user 30 needs to be in a sleep state with a high sleep depth several hours before the target time. As a result, the system 10 and the vehicle usage fee determination method according to the present embodiment can encourage the user 30 who pays a fee to drive the vehicle 20 to get sufficient sleep before boarding the vehicle 20.

Further, the wearable device 35 attached to the arm 31 of the user 30 estimates the wakefulness level of the user 30. Therefore, the system 10 according to the present embodiment can reduce a labor to be required for the user 30 to acquire the own wakefulness level.

Further, in the system 10 and the vehicle usage fee determination method according to the present embodiment, when the above special condition is satisfied, the fee determination unit 123 of the management server 12 sets the usage fee (correction fee) higher than when the special condition is not satisfied. Therefore, in the system 10 and the vehicle usage fee determination method according to the present embodiment, it is possible to encourage the user 30 who drives the vehicle 20 in a state of the low wakefulness level to temporarily stop driving the vehicle 20 to take a rest or switch to another driver.

Although the system 10 and the vehicle usage fee determination method according to the embodiment have been described above, the design of the system 10 and the vehicle usage fee determination method can be appropriately changed without departing from the scope of the present disclosure.

For example, the threshold value may be a wakefulness level other than the wakefulness level 1. For example, the threshold value may be the wakefulness level 2.

The first predetermined time does not have to be 20 minutes. For example, the first predetermined time may be five minutes.

The second predetermined time does not have to be five minutes. For example, the second predetermined time may be 10 minutes.

Further, data acquired by a device for estimating the wakefulness level of the user 30, the device being provided on the seat of the aircraft, may be transmitted from the wireless communication device provided on the seat to at least one of the mobile terminal 16 and the wireless communication device 13 of the management server 12.

In addition, a sleep state certificate (not shown) issued by an operating company of the aircraft may be photographed by a camera (not shown) provided in the wearable device 35, and the wakefulness level estimation unit 351 may estimate the wakefulness level of the user 30 based on the acquired image data.

The management server 12 may include a function corresponding to the wakefulness level estimation unit.

The car sharing company may own the system 10. For example, the management server 12 and the operation terminal 14 may be installed in a store of the car sharing company.

Instead of the GPS receiver 26, the vehicle 20 may include a receiver capable of receiving information from satellites of a global navigation satellite system (for example, Galileo) other than GPS.

What is claimed is:

1. A vehicle usage fee determination system comprising:
a reception unit that receives a usage application by a user who has an intention to drive a vehicle;
a wakefulness level estimation unit that estimates a wakefulness level of the user based on data received from a sensor configured to capture image data of the user;
a fee determination unit that sets a usage fee of the vehicle when a target wakefulness level that is the wakefulness level at a time a first predetermined time before a scheduled driving start time of the vehicle by the user is a predetermined value to be equal to or lower than a usage fee of the vehicle when the target wakefulness level is lower than the predetermined value; and
a warning generation unit configured to generate a warning in response to the wakefulness level being lower than the predetermined value, and in response to said warning, activate a speaker control unit configured to audibly relay said warning to the user or a display to output the warning to the user.

2. The vehicle usage fee determination system according to claim 1, wherein a wearable device that is able to be worn by the user includes the wakefulness level estimation unit.

3. The vehicle usage fee determination system according to claim 1, wherein in a case where a special condition to be satisfied when a state in which the wakefulness level of the user during driving the vehicle is lower than a predetermined threshold value continues for a second predetermined time or longer is satisfied, the fee determination unit sets the usage fee of the vehicle high as compared with a case where the special condition is not satisfied.

4. A vehicle usage fee determination method comprising:
a step of receiving a usage application by a user who has an intention to drive a vehicle;
a step of estimating a wakefulness level of the user based on data received from a sensor configured to capture image data of the user;
a step of setting a usage fee of the vehicle when a target wakefulness level that is the wakefulness level at a time a first predetermined time before a scheduled driving start time of the vehicle by the user is a predetermined value to be equal to or lower than a usage fee of the vehicle when the target wakefulness level is lower than the predetermined value; and
a step of generating a warning in response to the wakefulness level being lower than the predetermined value and in response to said warning, activating a speaker control unit configured to audibly relay said warning to the user instructing at least one of a speaker or a display to output the warning to the user.

5. The vehicle usage fee determination system according to claim 1, wherein the sensor comprises an in-vehicle camera configured to capture an image of the user.

6. The vehicle usage fee determination system according to claim 5, wherein the wakefulness level estimation unit estimates the wakefulness level based on a degree to which eyelids of the user are opening and on a cycle of opening and closing of the eyelids of the user.

7. The vehicle usage fee determination system according to claim 1, further comprising:
a speaker configured to output the warning received from the warning generation unit; and
a display configured to output the warning received from the warning generation unit.

8. The vehicle usage fee determination system according to claim 1, wherein the warning generation unit is configured to determine whether the vehicle has stopped based on data from the sensor, a wheel speed sensor, and a global position system (GPS) receiver.

9. The vehicle usage fee determination system according to claim 1, wherein the sensor comprises a wearable device configured to capture data from the user.

10. The vehicle usage fee determination system according to claim 9, wherein the data from the user comprises at least one of a heart rate of the user or a blood pressure of the user.

11. The vehicle usage fee determination system according to claim 9, wherein the wearable device is configured to wirelessly transmit the data from the user to the wakefulness estimation unit.

12. The vehicle usage fee determination system according to claim 9, wherein the wakefulness estimation unit is configured to wirelessly transmit the wakefulness level to the wearable device.

13. The vehicle usage fee determination system according to claim 1, further comprising a wireless control unit configured to wirelessly transmit the usage fee to a mobile device accessible by the user.

14. A vehicle usage fee determination system comprising:
a mobile device accessible by a user, wherein the mobile device comprises a display speaker and a display speaker control unit;
a reception unit that wirelessly receives, from the mobile device, a usage application by the user who has an intention to drive a vehicle;
a wakefulness level estimation unit that estimates a wakefulness level of the user based on data received from the reception unit;
a fee determination unit that sets a usage fee of the vehicle when a target wakefulness level that is the wakefulness level at a time a first predetermined time before a scheduled driving start time of the vehicle by the user is a predetermined value to be equal to or lower than a usage fee of the vehicle when the target wakefulness level is lower than the predetermined value; and
a warning generation unit configured to generate a warning in response to the wakefulness level being lower than the predetermined value and to wirelessly transmit the warning to the mobile device, and in response to said warning, activate the speaker control unit configured to audibly relay said warning to the user wherein the display control unit is configured to control the display to display the warning.

15. The vehicle usage fee determination system according to claim 14, further comprising an in-vehicle camera configured to capture image data of the user, wherein the wakefulness level estimation unit is configured to determine the wakefulness level based on the captured image data of the user.

16. The vehicle usage fee determination system according to claim 15, wherein the wakefulness level estimation unit estimates the wakefulness level based on a degree to which eyelids of the user are opening and on a cycle of opening and closing of the eyelids of the user.

17. The vehicle usage fee determination system according to claim 14, further comprising:
a speaker configured to output the warning received from the warning generation unit; and
a display configured to output the warning received from the warning generation unit.

18. The vehicle usage fee determination system according to claim 14, further comprising a wearable device configured to capture data from the user, wherein the wakefulness level estimation unit is configured to determine the wakefulness level based on the captured data from the user.

19. The vehicle usage fee determination system according to claim 18, wherein the data from the user comprises at least one of a heart rate of the user or a blood pressure of the user.

20. The vehicle usage fee determination system according to claim 18, wherein the wearable device is configured to wirelessly transmit the data from the user to the wakefulness estimation unit, and the wakefulness estimation unit is configured to wirelessly transmit the wakefulness level to the wearable device.

* * * * *